United States Patent
Park et al.

(10) Patent No.: US 10,197,509 B2
(45) Date of Patent: Feb. 5, 2019

(54) APPARATUS FOR PROCESSING SIGNAL BY MEANS OF ELECTROMAGNETIC WAVES AND METHOD FOR CONTROLLING THE APPARATUS

(71) Applicant: MUTRONICS CO., LTD., Anseong-si, Gyeonggi-do (KR)

(72) Inventors: Seung-Mo Park, Suwon-si (KR); Tae-Wook Lim, Suwon-si (KR); Jae-Hong Lim, Suwon-si (KR); Kwang-Won Lee, Suwon-si (KR); Sang-Jin Kim, Suwon-si (KR)

(73) Assignee: MUTRONICS CO., LTD., Anseong-si, Gyeonggi-Do (KR)

( * ) Notice: Subject to any disclaimer, the term of this patent is extended or adjusted under 35 U.S.C. 154(b) by 82 days.

(21) Appl. No.: 15/507,406

(22) PCT Filed: Oct. 5, 2015

(86) PCT No.: PCT/KR2015/010498
§ 371 (c)(1),
(2) Date: Feb. 28, 2017

(87) PCT Pub. No.: WO2016/068505
PCT Pub. Date: May 6, 2016

(65) Prior Publication Data
US 2017/0284946 A1 Oct. 5, 2017

(30) Foreign Application Priority Data

Oct. 31, 2014 (KR) .................. 10-2014-0150090
Sep. 25, 2015 (KR) .................. 10-2015-0136994

(51) Int. Cl.
*H01L 21/00* (2006.01)
*G01N 22/00* (2006.01)
(Continued)

(52) U.S. Cl.
CPC .......... *G01N 22/00* (2013.01); *G01R 29/0892* (2013.01); *G01R 1/00* (2013.01); *H01L 21/00* (2013.01); *H01L 2221/00* (2013.01)

(58) Field of Classification Search
CPC ........ H04B 1/00; H04B 2201/00; H01Q 1/00; H01P 1/00; G06T 1/00; G06T 2200/00; G06K 1/00; G06K 2207/00
See application file for complete search history.

(56) References Cited

U.S. PATENT DOCUMENTS 6,181,766 B1  1/2001  Pearson, Jr. et al.
7,671,784 B2  3/2010  Steinway et al.
(Continued)

FOREIGN PATENT DOCUMENTS

JP  2000-229077     8/2000
JP  2008-542759    11/2008
KR  10-2010-0007078  1/2010

OTHER PUBLICATIONS

Seong-Ho Son et al., "Preclinical Prototype Development of a Microwave Tomography System for Breast Cancer Detection" ETRI Journal, vol. 32, No. 6, Dec. 2010, pp. 901-910.
(Continued)

*Primary Examiner* — Jermele M Hollington
*Assistant Examiner* — Temilade Rhodes-Vivour
(74) *Attorney, Agent, or Firm* — Kile Park Reed & Houtteman PLLC (57) ABSTRACT

An apparatus for processing a signal by means of electromagnetic waves according to one embodiment of the present invention can, when a radio frequency (RF) signal is radiated onto a medium through any one of a plurality of channels, simultaneously receive the radiated RF signals which have been reflected or scattered by the medium or have penetrated the medium through the plurality of chan-
(Continued)

nels other than the channel through which the RF signal has been radiated.

15 Claims, 9 Drawing Sheets

(51) Int. Cl.
    *G01R 29/08*     (2006.01)
    *G01R 1/00*     (2006.01)

(56) References Cited

U.S. PATENT DOCUMENTS

| | | | |
|---|---|---|---|
| 2008/0103391 A1 | 5/2008 | Dos Santos Varela | |
| 2008/0231501 A1* | 9/2008 | Isaji | G01S 7/35 342/195 |
| 2008/0278370 A1* | 11/2008 | Lachner | G01S 7/03 342/200 |
| 2010/0010335 A1 | 1/2010 | Kim et al. | |
| 2011/0163906 A1* | 7/2011 | Yang | G01S 7/03 342/27 |
| 2011/0269408 A1* | 11/2011 | Brommer | G06K 1/00 455/67.11 |

OTHER PUBLICATIONS

International Search Report for International Application No. PCT/KR2015/010498, dated Feb. 5, 2016.

\* cited by examiner

APPARATUS FOR PROCESSING SIGNAL BY MEANS OF ELECTROMAGNETIC WAVES AND METHOD FOR CONTROLLING THE APPARATUS

TECHNICAL FIELD

The present invention relates to signal processing using electromagnetic waves.

BACKGROUND ART

Devices for examining a medium such as medical devices, mine detectors, geological survey equipment, etc. generally employ sensors for electromagnetic waves, ultrasonic waves, X-rays, and so on.

Among means of examining a medium, X-rays make use of a strongly linear feature thereof and a feature in that transmittance thereof varies according to components of a medium, but have a disadvantage in that they are harmful to a human body.

Ultrasonic waves and electromagnetic waves make use of a feature in that attenuation and propagation velocities thereof vary according to components of a medium and a fact that a feature, such as reflection, transmission, refraction, scattering, etc., appears at an interface between different kinds of media.

An existing device for measuring electromagnetic waves measures electromagnetic waves using a single transceiver and a switching matrix while sequentially changing reception channels. Therefore, there is a disadvantage in that a measurement time is long.

A related technology is, for example, Korean Patent Publication No. 2010-0007078 ("Apparatus and method for cancer detection using electromagnetic waves," publication date: Jan. 22, 2010).

DISCLOSURE

Technical Problem

The present invention is directed to providing an apparatus for processing a signal using electromagnetic waves which makes it possible to omit a complex switching matrix and also significantly reduce a measurement time.

Technical Solution

One aspect of the present invention provides a signal processing apparatus having a plurality of channels, each of the plurality of channels including: an antenna configured to radiate a radio frequency (RF) signal toward a medium in a transmission mode and receive an RF signal reflected or scattered by the medium or penetrating the medium in a reception mode; and a transceiver module configured to generate and transfer the RF signal to the antenna in the transmission mode and detect a phase and an amplitude of the RF signal received by the antenna in the reception mode, wherein, when the RF signal is radiated toward the medium through any one of the plurality of channels, radiated RF signals reflected or scattered by the medium or penetrating the medium are simultaneously received through the plurality of channels other than the channel through which the RF signal has been radiated.

Another aspect of the present invention provides a signal processing method using a plurality of channels, the method including: a first operation of, when a water tank is filled with a liquid and an RF signal is radiated toward the liquid through any one of the plurality of channels, receiving radiated RF signals reflected or scattered by the liquid or an RF signal transmitted through the liquid through the plurality of channels other than the channel through which the RF signal has been radiated, and generating first data including a phase and an amplitude of the received RF signal; a second operation of, when a medium is inserted into the water tank filled with the liquid and the RF signal is radiated toward the medium through any one of the plurality of channels, receiving radiated RF signals reflected or scattered by the medium or penetrating the medium through the plurality of channels other than the channel through which the RF signal has been radiated, and generating second data including a phase and an amplitude of the received RF signal; and a third operation of calculating permittivity and conductivity information of the medium based on a difference between the first data and the second data, wherein the RF signal reflected or scattered by the liquid or the medium or transmitted through the liquid is simultaneously received through all of the plurality of channels other than the channel through which the RF signal has been radiated.

Advantageous Effects

According to an exemplary embodiment of the present invention, when a radio frequency (RF) signal is radiated through any one of a plurality of channels, radiated RF signals reflected or scattered by the medium or penetrating the medium are simultaneously received through the remaining channels. Therefore, it is possible to omit a complex switching matrix and also significantly reduce a measurement time.

Further, according to another exemplary embodiment of the present invention, a plurality of transceiver modules are simultaneously provided with a reference clock and/or a sampling clock to be synchronized with each other. Therefore, it is possible to improve accuracy and stability of measurement.

MODES OF THE INVENTION

Hereinafter, exemplary embodiments of the present invention will be described with reference to the accompanying drawings. However, embodiments of the present invention may be modified in various other forms, and the scope of the present invention is not limited to exemplary embodiments described below. Throughout the drawings, shapes, sizes, etc. of elements may be exaggerated for clarity, and elements indicated by the same reference sign are identical elements.

Figure 1:
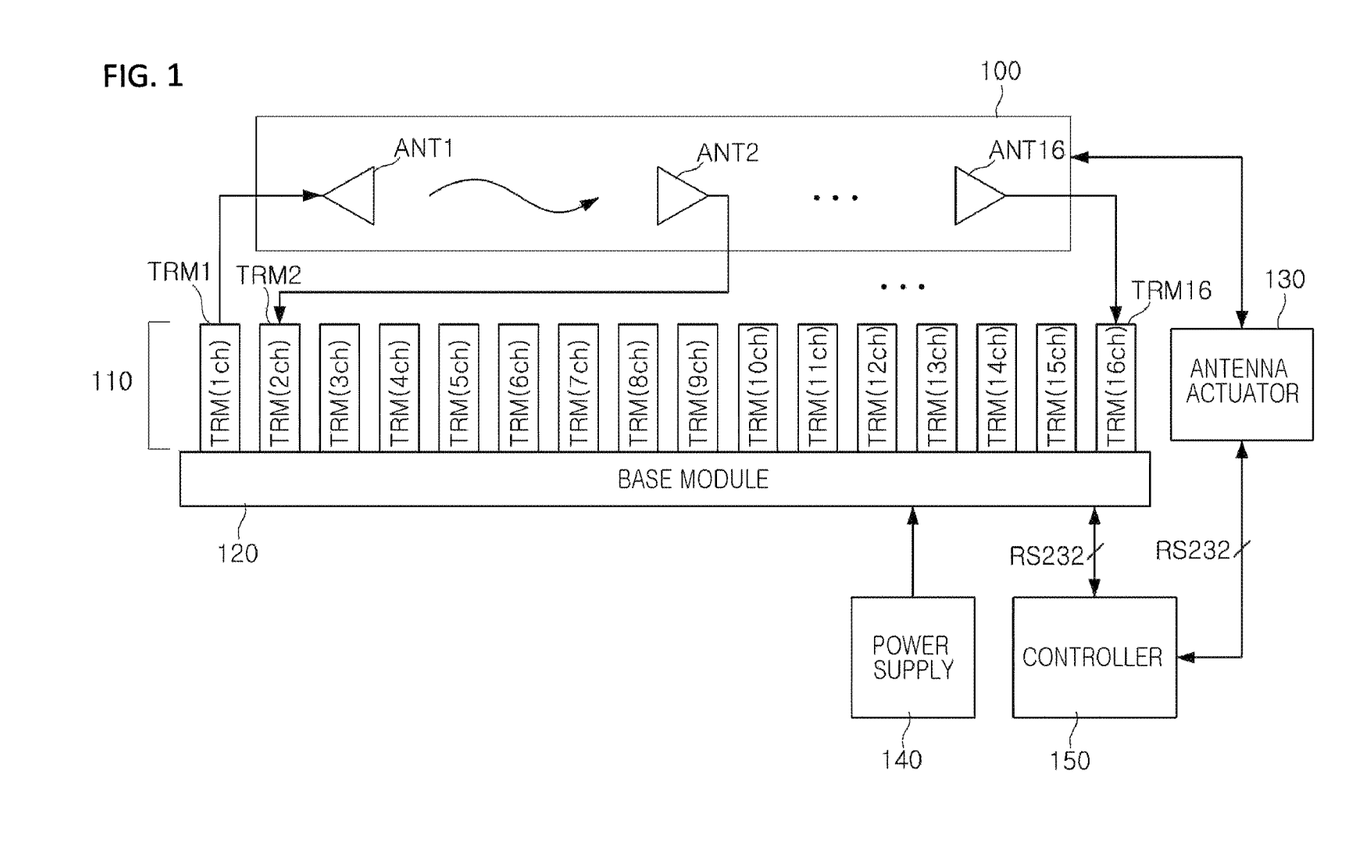
FIG. 1 is a diagram showing a configuration of an apparatus for processing a signal using electromagnetic waves according to an exemplary embodiment of the present invention.
Figure 2:
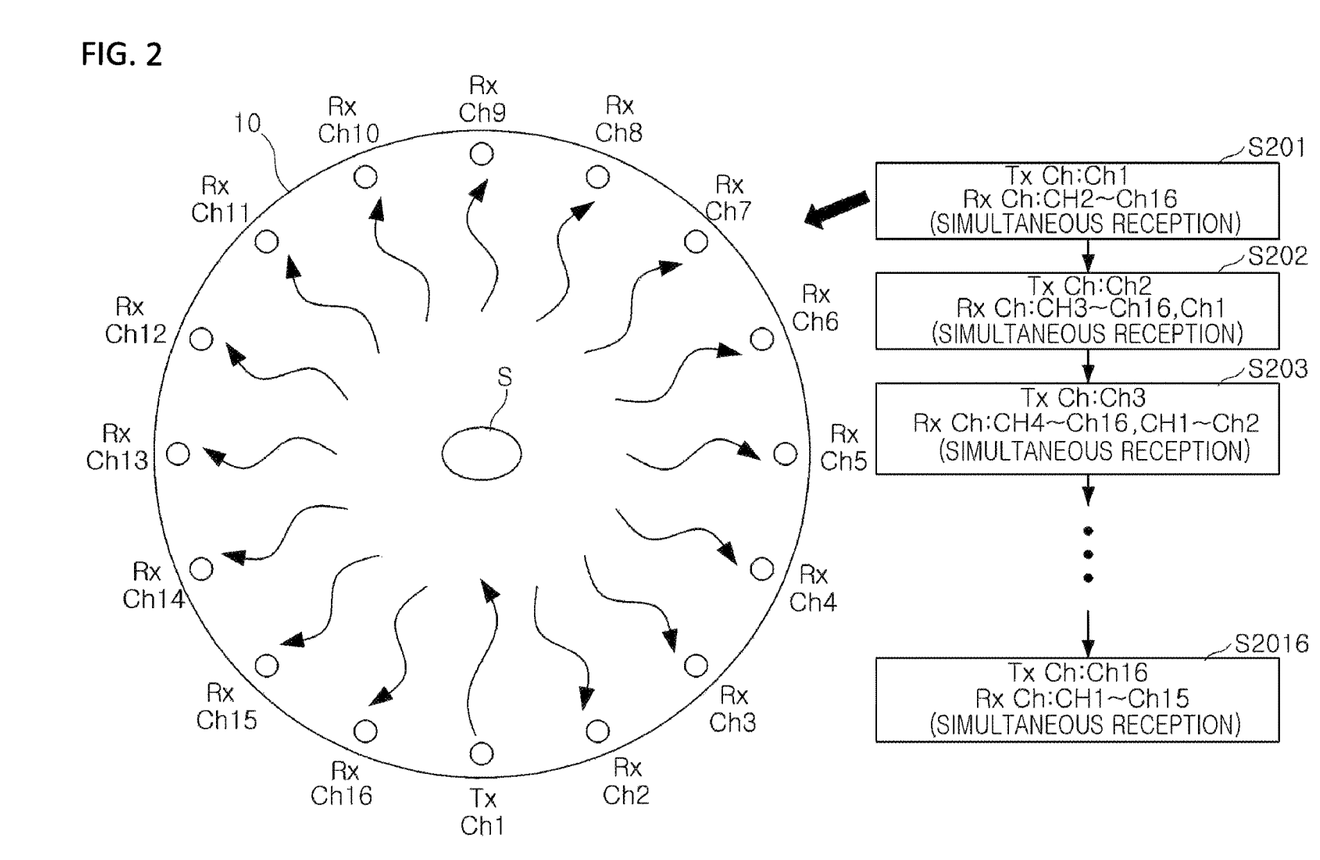
FIG. 2 is a diagram illustrating transmission and reception of a radio frequency (RF) signal according to an exemplary embodiment of the present invention.

FIG. 1 is a diagram showing a configuration of an apparatus for processing a signal using electromagnetic waves according to an exemplary embodiment of the present invention. FIG. 2 is a diagram illustrating transmission and reception of a radio frequency (RF) signal according to an exemplary embodiment of the present invention, and FIG. 3 is a diagram showing antennas disposed along a circumference of a water tank and a direction of movement of the antennas caused by an actuator according to an exemplary embodiment of the present invention.

First, as shown in FIG. 1, an apparatus for processing a signal according to an exemplary embodiment of the present invention may include an antenna unit 100 including a plurality of antennas ANT1 to ANT16, a transceiver unit 110 including a plurality of transceiver modules TRM1 to TRM16, a base module 120, an antenna actuator 130, a power supply 140, and a controller 150. The controller 150 and the base module 120 may be connected by a Recommended Standard 232 (RS232) cable, and this is the same for the controller 150 and the antenna actuator 130.

Figure 3:
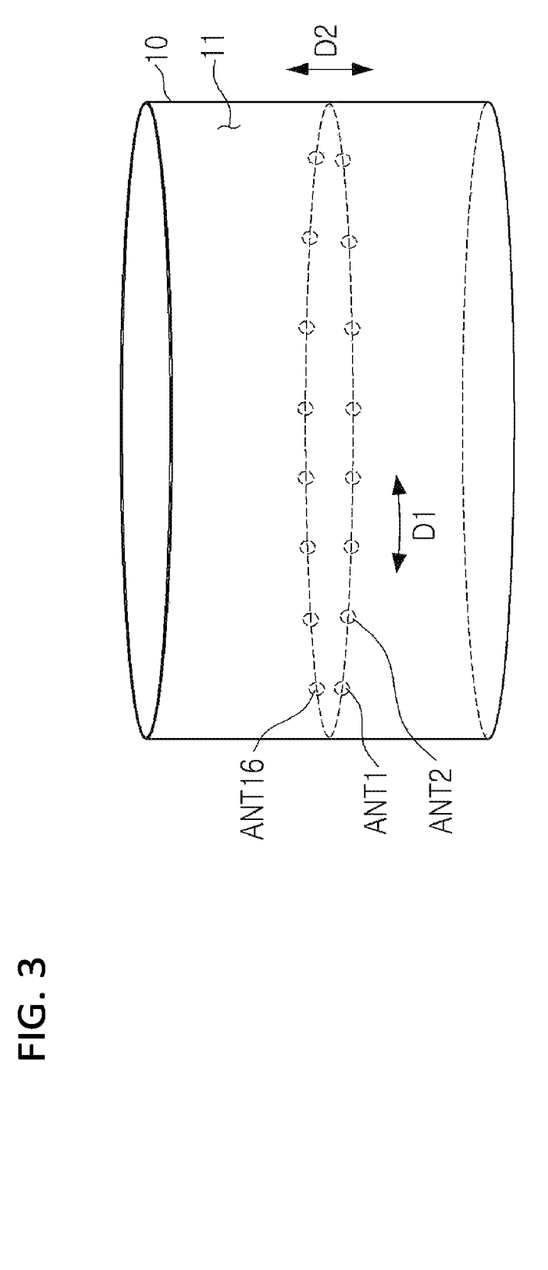
FIG. 3 is a diagram showing antennas disposed along a circumference of a water tank and a direction of movement of the antennas caused by an actuator according to an exemplary embodiment of the present invention.

As shown in FIG. 3, the plurality of antennas ANT1 to ANT16 may be disposed to have the same angle therebetween along a circumference of a water tank 10, and the water tank 10 may be filled with a liquid 11 having the same permittivity as a medium.

Meanwhile, in a description of an exemplary embodiment of the present invention, the term "channel" includes one antenna and one transceiver module. For example, a first channel 1ch includes the first antenna ANT1 and the first transceiver module TRM1, a second channel ch2 includes the second antenna ANT2 and the second transceiver module TRM2, and a sixteenth channel 16ch includes the sixteenth antenna ANT16 and the sixteenth transceiver module TRM16. Although FIG. 1 shows sixteen channels and is intended to aid in understanding the present invention, it should be noted that the number of channels may be more or less than sixteen according to the necessity of those of ordinary skill in the art.

Specifically, each of a plurality of channels may include an antenna which radiates an RF signal toward a medium in a transmission mode and receives an RF signal reflected or scattered by the medium or penetrating the medium in a reception mode, and a transceiver module which generates and transfers the RF signal to the antenna in the transmission mode and detects a phase and an amplitude of the RF signal received by the antenna in the reception mode.

In particular, according to an exemplary embodiment of the present invention, when an RF signal is radiated toward a medium through any one of a plurality of channels, radiated RF signals reflected or scattered by the medium or penetrating the medium may be simultaneously received through the plurality of channels other than the channel through which the RF signal has been radiated.

Specifically, as shown in FIG. 2, the sixteen channels ch1 to ch16 are configured so that an RF signal is radiated toward a medium S through the first channel ch1 and RF signals reflected or scattered by the medium S or penetrating the medium S are simultaneously received through the remaining channels ch2 to ch16 (S201). Subsequently, the sixteen channels ch1 to ch16 are configured so that an RF signal is radiated toward the medium S through the second channel ch2 and RF signals reflected or scattered by the medium S or penetrating the medium S are simultaneously received through the remaining channels ch1 and ch3 to ch16 (S202).

Subsequently, the sixteen channels ch1 to ch16 are configured so that an RF signal is radiated toward the medium S through the third channel ch3 and RF signals reflected or scattered by the medium S or penetrating the medium S are simultaneously received through the remaining channels ch1, ch2, and ch4 to ch16 (S203). This is sequentially performed until an RF signal is transmitted through the last channel, that is, the sixteenth channel ch16 (S2016).

Meanwhile, in each of operations S201 to S2016, a frequency of the radiated RF signal has a frequency range of 3 GHz to 6 GHz, and a unit of frequency change may be adjusted to be an arbitrary value, such as 500 MHz, 1 GHz, and the like.

In this way, radiation and reception of an RF signal may be performed for all of the plurality of channels in sequence. In FIG. 2, an unmentioned reference sign "10" indicates the water tank, and "Tx ch" and "Rx ch" denote a transmission channel and a reception channel, respectively.

According to an exemplary embodiment of the present invention described above, assuming that a unit of frequency sweep is 1 GHz, the number of measurement times of an existing sequential reception method is the number of Tx channels (16)×the number of measurement times of Rx channels (15)×frequency sweeps (4)=960,whereas the number of measurement times of an exemplary embodiment of the present invention is the number of Tx channels (16)×the number of measurement times of Rx channels (1)×frequency sweeps (4) =64. Therefore, there is an advantage in that a time required for the existing method can be significantly reduced.

Meanwhile, the base module 120 may be configured to divide a reference clock and/or a sampling clock according to the number of the plurality of channels ch1 to ch16 and simultaneously provide the divided reference clock and/or sampling clock to the plurality of transceiver modules TRM1 to TRM16 to synchronize the plurality of transceiver modules TRM1 to TRM16.

As shown in FIG. 3, the antenna actuator 130 may rotate each of the antennas ANT1 to ANT16 separately included in the plurality of channels by a predetermined angle (see D1) about the medium S or move each of the antennas ANT1 to ANT16 a predetermined distance upward or downward on the water tank 10 (see D2) under control of the controller 150.

The power supply 140 may supply power to the base module 120 described above as a power supply.

Lastly, the controller 150 may control the transceiver unit 110 and the antenna actuator 130 and calculate permittivity and conductivity information by applying an inverse scattering interpretation program to output data (phases and frequencies of RF signals) of the transceiver unit 110.

Figure 4:
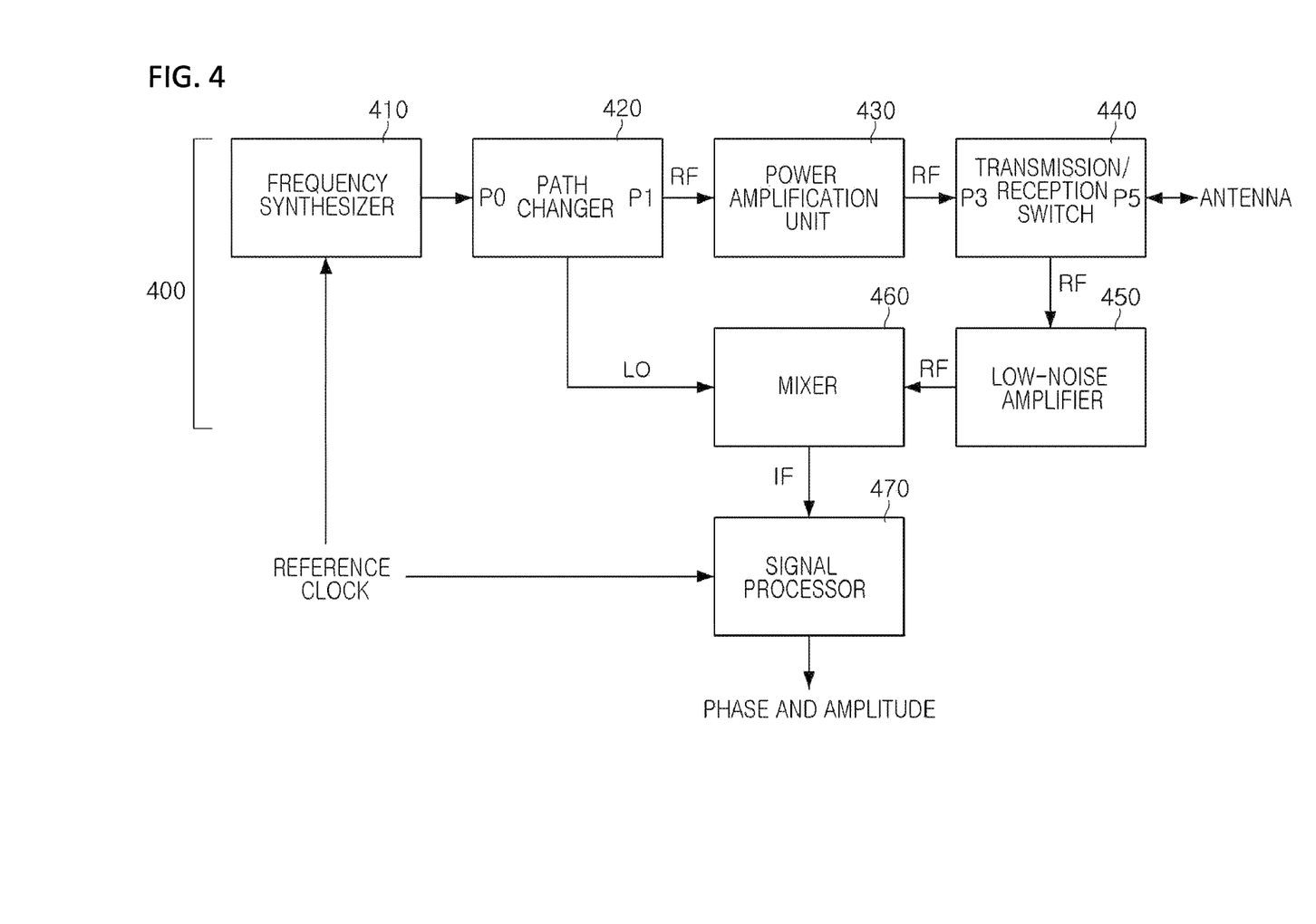
FIG. 4 is an internal block diagram of a transceiver module according to an exemplary embodiment of the present invention.
Figure 5:
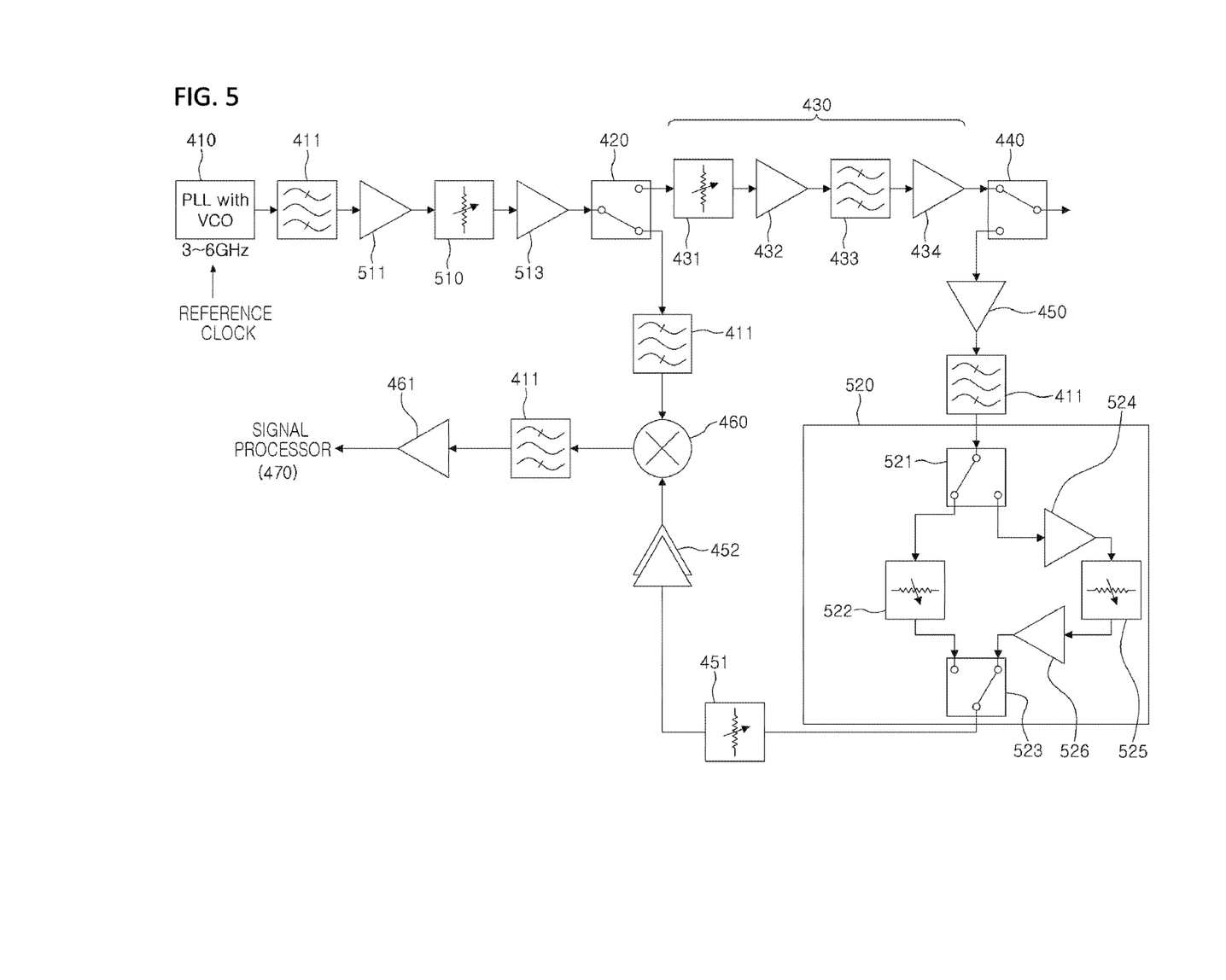
FIG. 5 is a diagram showing actual elements used in an RF unit of a transceiver module according to an exemplary embodiment of the present invention.

Meanwhile, FIG. 4 is an internal block diagram of a transceiver module according to an exemplary embodiment of the present invention, and FIG. 5 is a diagram showing actual elements used in an RF unit of a transceiver module according to an exemplary embodiment of the present invention.

As shown in FIG. 4, each of the plurality of transceiver modules TRM1 to TRM16 may include an RF unit 400 and a signal processor 470. The RF unit 400 may radiate an RF signal RF generated based on a reference clock having a reference frequency toward a medium in the transmission mode, and generate an intermediate frequency signal IF from the RF signal RF received by an antenna in the reception mode.

Specifically, as shown in FIGS. 4 and 5, the RF unit 400 may include a frequency synthesizer 410 which generates an RF signal and a local oscillation signal LO from a reference frequency of a reference signal, a path changer 420 which transfers the RF signal RF to a power amplification unit 430 in the transmission mode and transfers the local oscillation signal LO to a mixer 460 in the reception mode, the power amplification unit 430 which amplifies the RF signal RF in the transmission mode, a low-noise amplifier 450 which amplifies the RF signal RF received in the reception mode, a transmission/reception switch which transfers the RF signal RF amplified by the power amplification unit 430 to the antenna in the transmission mode and transfers the RF signal RF received by the antenna to the low-noise amplifier 450 in the reception mode, and the mixer 460 which generates the intermediate frequency signal IF by mixing the local oscillation signal LO and the received RF signal RF in the reception mode.

In FIG. 5, a maximum amplitude of a transmission signal is set to 25 dBm and has no influence on a human body and a minimum amplitude of a reception signal is set to −125 dBm so that a dynamic range (a value obtained by subtracting the minimum amplitude of a reception signal from the maximum amplitude of a transmission signal) is set to 150 dB to satisfy requirements of a transceiver module. Here, the maximum amplitude of a transmission signal and the minimum amplitude of a reception signal may be increased or decreased according to conditions of measurement.

According to an exemplary embodiment of the present invention, as shown in FIG. 5, a transmission signal variation unit 510 may be further provided between the frequency synthesizer 410 and the path changer 420, and a reception signal variation unit 520 may be further provided between the low-noise amplifier 450 and the mixer 460.

The transmission signal variation unit 510 may include an attenuator 512 and attenuate an RF signal to be radiated toward the medium S in the transmission mode, and the reception signal variation unit 520 may include switches 521 and 523, an attenuator 522, and two low-noise amplifiers 522 and 525 and properly change an amplitude of the received RF signal in the reception mode.

In particular, according to an exemplary embodiment of the present invention, a path is changed according to the amplitude of the received RF signal. When the amplitude is large, the RF signal is passed through only the attenuator 512 on the left side to be properly attenuated, and when the amplitude is small, the RF signal is passed through the attenuator 522 and the two low-noise amplifiers 522 and 525 on the right side to be attenuated and also amplified. It should be noted that the two low-noise amplifiers 522 and 525 may be configured as one noise amplifier according to performance.

Meanwhile, in FIG. 5, the power amplification unit 430 is configured with two amplifiers 432 and 434, an attenuator 431, and a filter 433, and an unmentioned reference sign "411" indicates a filter, and unmentioned reference signs "511, 513, 452, and 461" indicate amplifiers. The aforementioned switches 420, 440, 521, and 523 may be implemented as single pole double throw (SPDT) switches.

The signal processor 470 may convert an intermediate frequency signal into a digital signal based on a sampling block having a sampling frequency and detect a phase and an amplitude of the converted digital signal. The detected phase and amplitude may be transferred to the controller 150 and used to calculate permittivity and conductivity information of the medium S.

Figure 6:
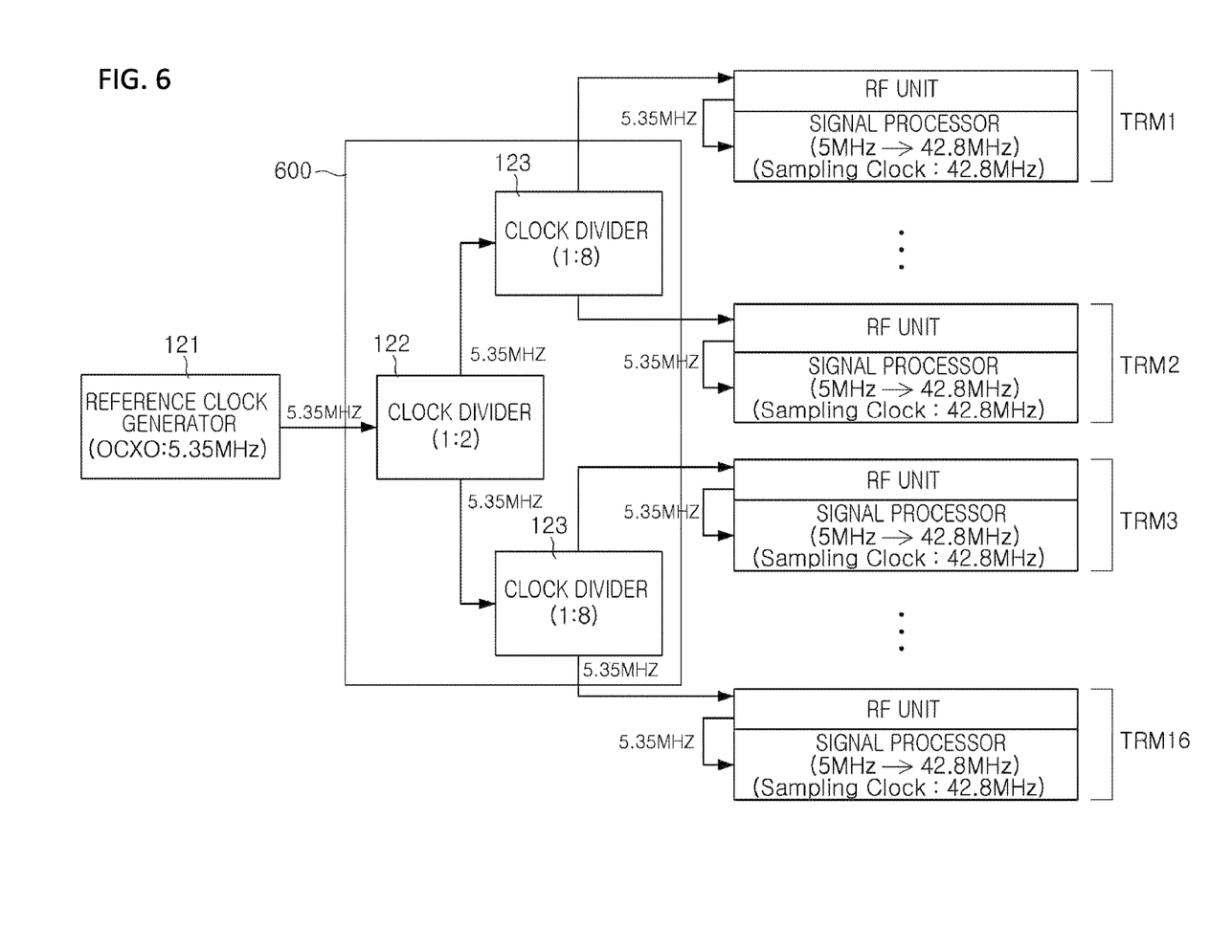
FIG. 6 is a diagram showing a method of providing a reference clock and a sampling clock to transceiver modules according to an exemplary embodiment of the present invention.

FIG. 6 is a diagram showing a method of providing a reference clock and a sampling clock to transceiver modules according to an exemplary embodiment of the present invention.

As shown in FIG. 6, the base module 120 (see FIG. 1) may include a reference clock generator 121 and a reference clock divider module 600.

Specifically, the reference clock generator 121 may generate a reference clock having a reference frequency of 5.35 MHz using an oven-controlled crystal oscillator (OXCO), and the generated reference clock may be divided by the reference clock divider module 600 and simultaneously provided to a plurality of RF units TRM1 to TRM16 so that the plurality of RF units TRM1 to TRM16 may be synchronized. The aforementioned reference clock divider module 600 may include one 1:2 clock divider 122 and two 1:8 clock dividers 123.

Subsequently, the plurality of RF units TRM1 to TRM16 may generate sampling clocks having a sampling frequency of 42.8 MHz based on the reference clock therein and transfer the generated sampling clocks to signal processors thereof.

Figure 7:
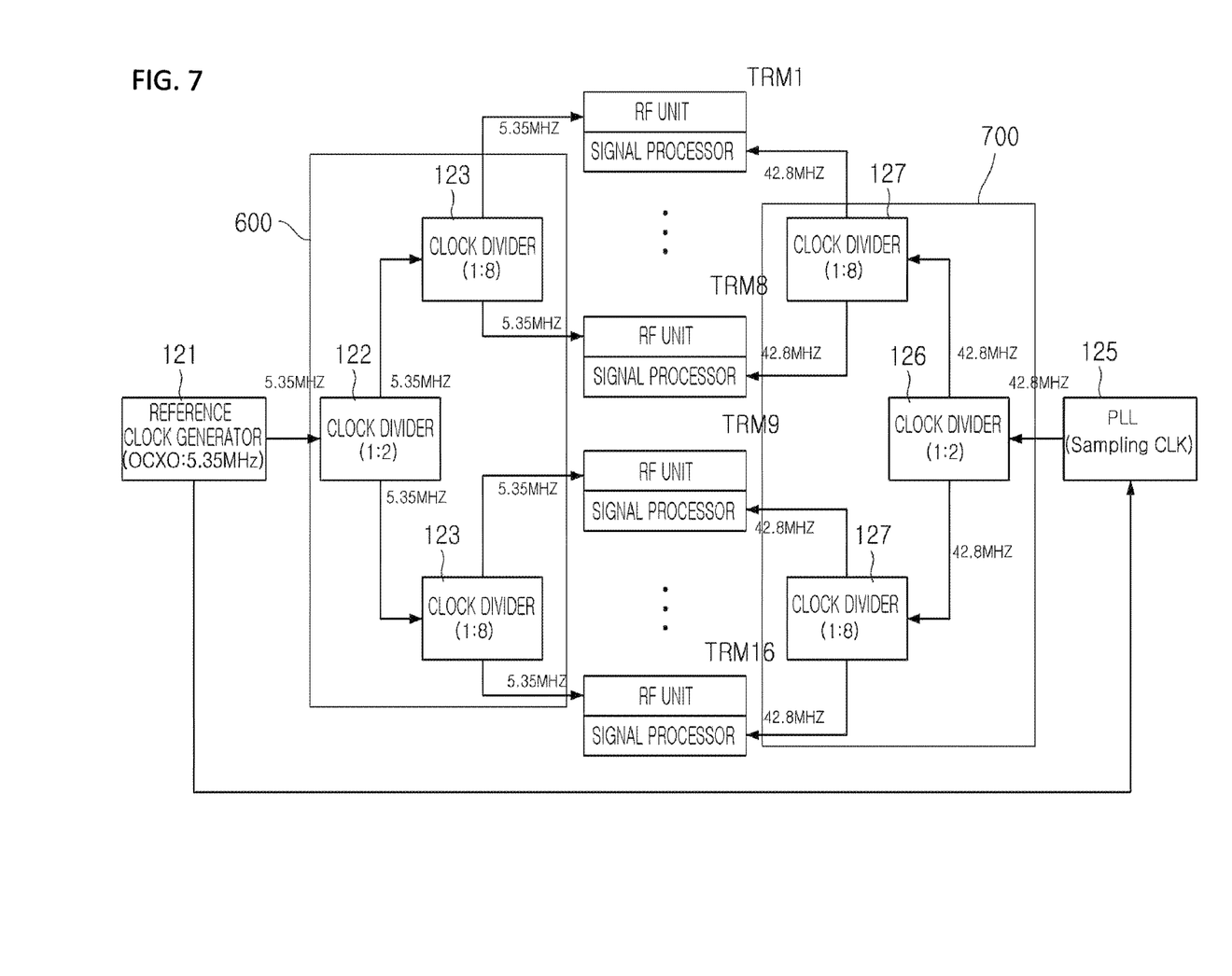
FIG. 7 is a diagram illustrating a method of providing a reference clock and a sampling clock to transceiver modules according to another exemplary embodiment of the present invention.

FIG. 7 is a diagram illustrating a method of providing a reference clock and a sampling clock to transceiver modules according to another exemplary embodiment of the present invention. Unlike FIG. 6, a sampling clock is also configured to be transferred to signal processors through a separate clock divider module.

In other words, a phase-locked loop (PLL) 125 receives a reference clock generated by the reference clock generator 121 and generates a sampling clock having a sampling frequency of 42.8 MHz, and the generated sampling clock is divided by a sampling clock divider module 700 and simultaneously provided to a plurality of signal processors. Therefore, the plurality of signal processors may be synchronized, and it is possible to improve accuracy and stability of measurement. The aforementioned sampling clock divider module 700 may include one 1:2 clock divider 126 and two 1:8 clock dividers 127.

It should be noted that detailed values shown in FIGS. 6 and 7 described above are merely intended to aid in understanding the present invention and may be changed as necessary.

Figure 8:
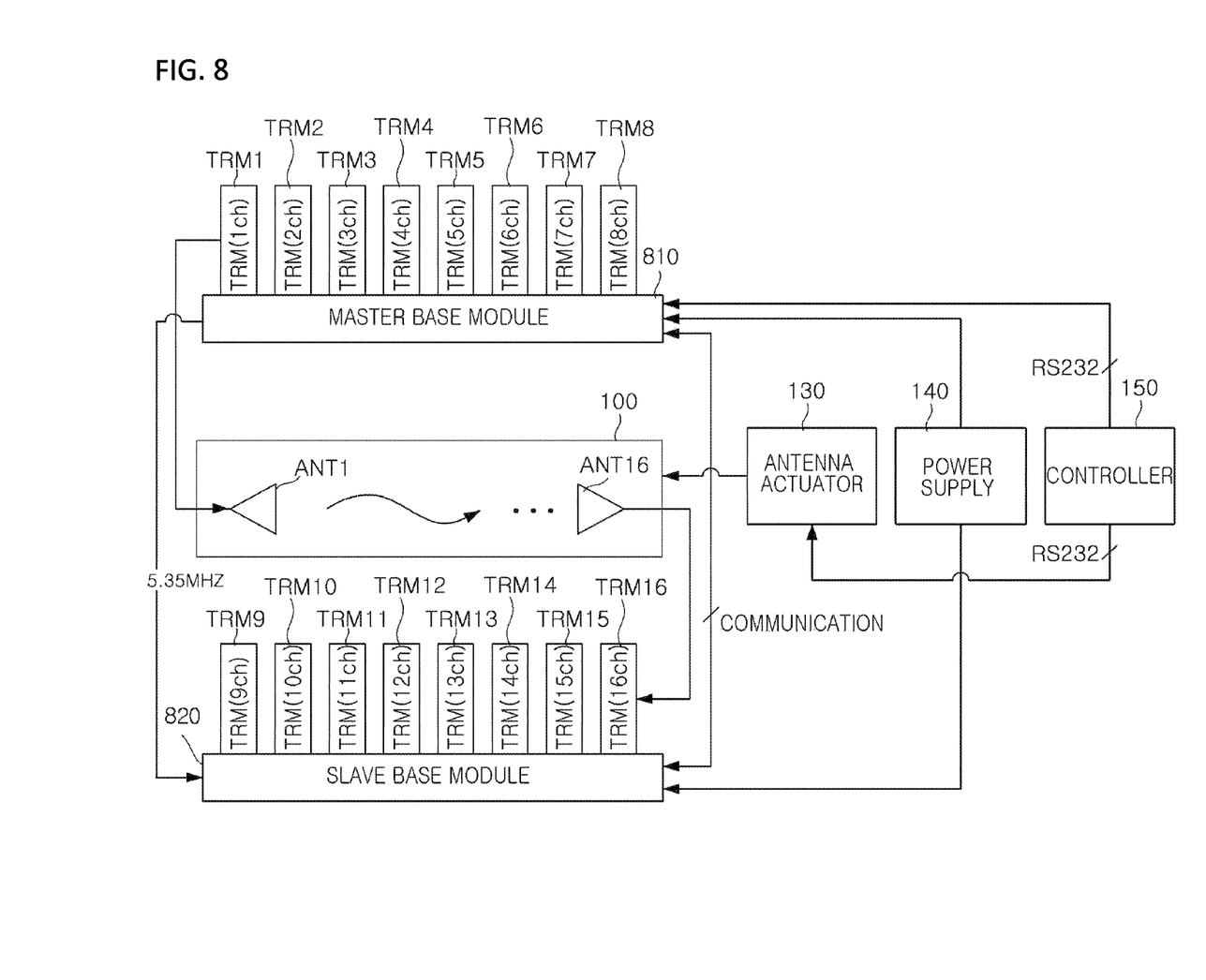
FIG. 8 is a diagram showing a configuration of an apparatus for processing a signal using electromagnetic waves according to an exemplary embodiment of the present invention.

FIG. 8 is a diagram showing a configuration of an apparatus for processing a signal using electromagnetic waves according to another exemplary embodiment of the present invention.

Unlike FIG. 1, one base module is divided into a master base module 810 and a slave base module 820. Eight transceiver modules TRM1 to TRM8 are connected to the master base module 810, and eight transceiver modules TRM9 to TRM16 are connected to the slave base module 820 so that the master base module 810 and the slave base module 820 are configured to be provided with a reference clock and/or a sampling clock. In this case, the master base module 810 may include the reference clock generator 121 and the upper 1:8 clock divider 123 in the reference clock divider module 600, and the slave base module 820 may include the lower 1:8 clock divider 123.

As described above, according to an exemplary embodiment of the present invention, when an RF signal is radiated toward a medium through any one of a plurality of channels, radiated RF signals reflected or scattered by the medium or an RF signal penetrating the medium are simultaneously received through the remaining channels. Therefore, it is possible to omit a complex switching matrix and also significantly reduce a measurement time.

Figure 9:
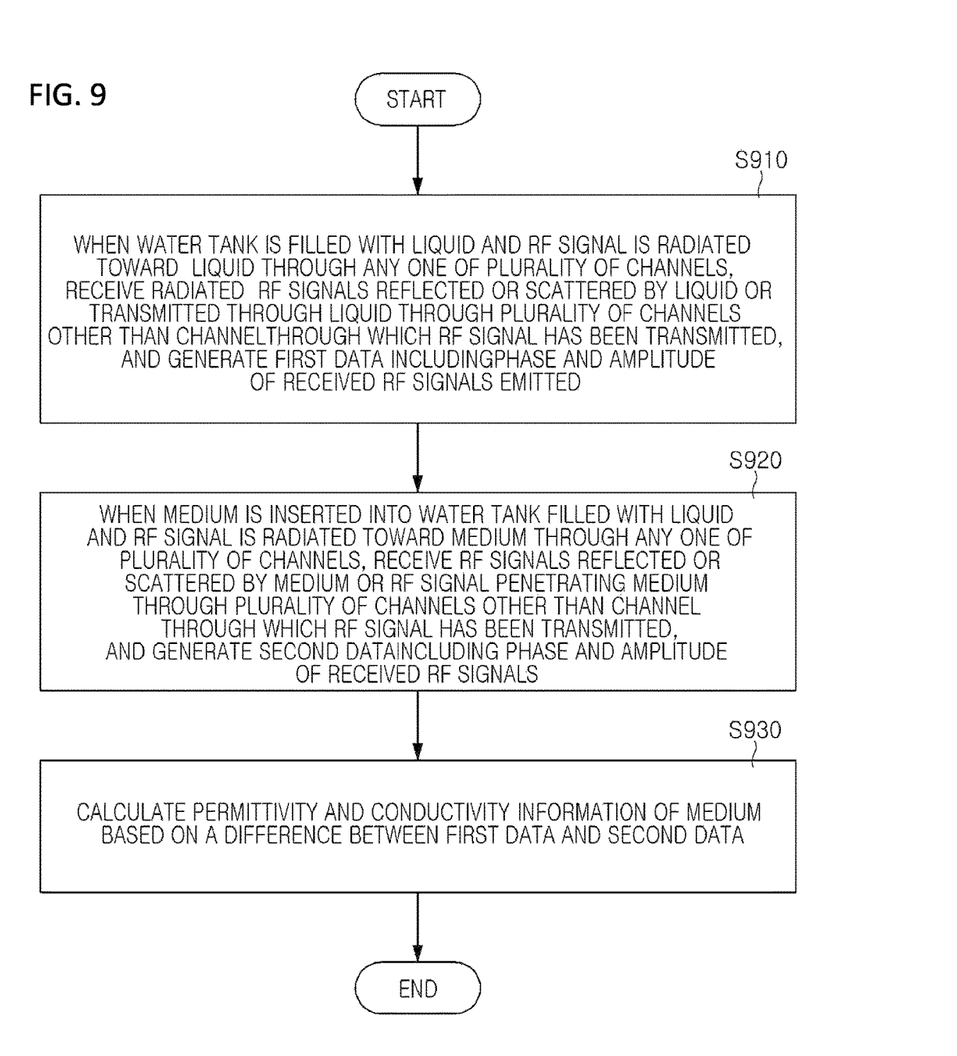
FIG. 9 is a flowchart illustrating a method of processing a signal using electromagnetic waves according to an exemplary embodiment of the present invention.

FIG. 9 is a flowchart illustrating a method of processing a signal using electromagnetic waves according to an exemplary embodiment of the present invention. To clarify the present invention, the same descriptions as made with reference to FIGS. 1 to 8 will be omitted.

As shown in FIG. 9, first, when a water tank is filled with a liquid and an RF signal is radiated toward the liquid through any one of a plurality of channels, radiated RF signals reflected or scattered by the liquid or an RF signal transmitted through the liquid are received through the plurality of channels other than the channel through which the RF signal has been radiated, and first data including a phase and an amplitude of the received RF signal is generated (S910).

Next, when a medium is inserted into the water tank filled with the liquid and an RF signal is radiated toward the medium through any one of the plurality of channels, radiated RF signals reflected or scattered by the medium or an RF signal penetrating the medium is received through the plurality of channels other than the channel through which the RF signal has been radiated, and second data including a phase and an amplitude of the received RF signal is generated (S920).

Finally, permittivity and conductivity information of the medium may be calculated based on a difference between the first data and the second data (S930).

According to an exemplary embodiment of the present invention, as described above, operations S910 and S920 may be sequentially performed for each of the plurality of channels, and a frequency of the RF signal radiated toward the medium may be swept at preset frequency intervals within a predetermined frequency range.

Also, according to an exemplary embodiment of the present invention, the above-described method of processing a signal may further include an operation of rotating each antenna separately included in the plurality of channels by a predetermined angle about the medium or moving each of the antennas a predetermined distance upward or downward on the water tank and then performing the second operation as described above.

As described above, according to an exemplary embodiment of the present invention, when an RF signal is radiated toward a medium through any one of a plurality of channels, a radiated RF signal reflected or scattered by the medium or an RF signal penetrating the medium is simultaneously received through the remaining channels. Therefore, it is possible to omit a complex switching matrix and also significantly reduce a measurement time.

The present invention is not limited to the exemplary embodiment described above and the appended drawings. The scope of the present invention is limited by the following claims, and it should be apparent to those of ordinary skill in the art that a variety of modifications and changes may be made without departing from the technical spirit of the present invention.

The invention claimed is:

1. A signal processing apparatus comprising a plurality of channels, wherein each of the plurality of channels comprises:
   an antenna configured to radiate a radio frequency (RF) signal toward a medium in a transmission mode and receive an RF signal reflected or scattered by the medium or penetrating the medium in a reception mode; and
   a transceiver module configured to generate and transfer the RF signal to the antenna in the transmission mode and detect a phase and an amplitude of the RF signal received by the antenna in the reception mode,
   wherein, when the RF signal is radiated toward the medium through any one of the plurality of channels, radiated RF signals reflected or scattered by the medium or penetrating the medium are simultaneously received through the plurality of channels other than the channel through which the RF signal has been radiated,
   wherein the transceiver module comprises:
   an RF unit configured to radiate the RF signal generated based on a reference frequency toward the medium in the transmission mode, and generate an intermediate frequency signal from the RF signal received by the antenna in the reception mode; and
   a signal processor configured to convert the generated intermediate frequency signal into a digital signal based on a sampling frequency and detect a phase and an amplitude of the converted digital signal.

2. The signal processing apparatus of claim 1, wherein the RF unit comprises:
   a frequency synthesizer configured to generate the RF signal and a local oscillation signal from the reference frequency;
   a power amplification unit configured to amplify the generated RF signal in the transmission mode;
   a low-noise amplifier configured to amplify the received RF signal in the reception mode; and
   a mixer configured to generate the intermediate frequency signal by mixing the local oscillation signal and the received RF signal in the reception mode.

3. The signal processing apparatus of claim 2, wherein the RF unit further comprises:
   a path changer configured to transfer the RF signal to the power amplification unit in the transmission mode and transfer the local oscillation signal to the mixer in the reception mode; and
   a transmission/reception switch configured to transfer the RF signal amplified by the power amplification unit to the antenna in the transmission mode and transfer the RF signal received by the antenna to the low-noise amplifier in the reception mode.

4. The signal processing apparatus of claim 2, wherein the RF unit further comprises:
   a transmission signal variation unit configured to attenuate an amplitude of the RF signal to be radiated toward the medium in the transmission mode; and
   a reception signal variation unit configured to change an amplitude of the received RF signal in the reception mode.

5. The signal processing apparatus of claim 4, wherein the reception signal variation unit only attenuates the amplitude of the received RF signal or attenuates and also amplifies the amplitude according to the amplitude of the received RF signal.

6. The signal processing apparatus of claim 1, further comprising a base module comprising:
- a reference clock generator configured to generate a reference clock having the reference frequency; and
- a reference clock divider module configured to synchronize a plurality of RF units by dividing the generated reference clock according to a number of the plurality of channels and simultaneously providing the divided reference clock to the plurality of RF units.

7. The signal processing apparatus of claim 6, wherein each of the plurality of RF units generates a sampling clock having a sampling frequency from the reference clock and provides the generated sampling clock to the signal processor.

8. The signal processing apparatus of claim 1, further comprising a base module comprising:
- a phase-locked loop (PLL) configured to generate a sampling clock having a sampling frequency from the reference clock; and
- a sampling clock divider module configured to synchronize a plurality of signal processors by dividing the generated sampling clock according to a number of the plurality of channels and simultaneously providing the divided sampling clock to the plurality of signal processors.

9. The signal processing apparatus of claim 1, wherein radiation and reception of the RF signal are performed for all of the plurality of channels in sequence.

10. The signal processing apparatus of claim 1, wherein a frequency of the RF signal radiated toward the medium is swept at preset frequency intervals within a predetermined frequency range.

11. A method of processing a signal using a plurality of channels, the method comprising:
- a first operation of, when a water tank is filled with a liquid and a radio frequency (RF) signal is radiated toward the liquid through any one of the plurality of channels, receiving radiated RF signals reflected or scattered by the liquid or an RF signal transmitted through the liquid through the plurality of channels other than the channel through which the RF signal has been radiated, and generating first data including phases and amplitudes of the received RF signals;
- a second operation of, when a medium is inserted into the water tank filled with the liquid and the RF signal is radiated toward the medium through any one of the plurality of channels, receiving radiated RF signals reflected or scattered by the medium or an RF signal penetrating the medium through the plurality of channels other than the channel through which the RF signal has been radiated, and generating second data including phases and amplitudes of the received RF signals; and
- a third operation of calculating permittivity and conductivity information of the medium based on a difference between the first data and the second data,
- wherein the RF signals reflected or scattered by the liquid or the medium or transmitted through the liquid are simultaneously received through all of the plurality of channels other than the channel through which the RF signal has been radiated.

12. The method of claim 11, wherein each of the plurality of channels comprises:
- an antenna configured to radiate the RF signal toward the liquid or the medium in a transmission mode and receive RF signals reflected or scattered by the liquid or the medium or transmitted through the liquid or the medium in a reception mode; and
- a transceiver module configured to generate and transfer the RF signal to the antenna in the transmission mode and detect the phase and the amplitude of the RF signal received by the antenna in the reception mode.

13. The method of claim 11, wherein the first operation and the second operation are performed for all of the plurality of channels in sequence.

14. The method of claim 11, wherein a frequency of the RF signal radiated toward the medium is swept at preset frequency intervals within a predetermined frequency range.

15. The method of claim 11, further comprising an operation of rotating each antenna separately included in the plurality of channels by a predetermined angle about the medium or moving each of the antennas a predetermined distance upward or downward on the water tank and then performing the second operation.

* * * * *